United States Patent [19]

Takagi

[11] Patent Number: 5,103,472
[45] Date of Patent: Apr. 7, 1992

[54] X-RAY IMAGING APPARATUS

[75] Inventor: Michio Takagi, Tochigi, Japan

[73] Assignee: Kabushiki Kaisha Toshiba, Kawasaki, Japan

[21] Appl. No.: 571,866

[22] Filed: Aug. 24, 1990

[30] Foreign Application Priority Data

Aug. 28, 1989 [JP] Japan .................................. 1-221343

[51] Int. Cl.⁵ .................................................... H05G 1/02
[52] U.S. Cl. .................................. 378/197; 378/193; 378/198; 378/189
[58] Field of Search ............... 378/197, 198, 196, 193, 378/195, 189; 74/526, 527; 248/289.1, 417, 418, 145, 407, 408, 231.3, 425

[56] References Cited

U.S. PATENT DOCUMENTS

3,774,470 11/1973 Cottin .................................. 74/527
4,919,383 4/1990 Benjamin et al. ................. 248/417

Primary Examiner—Janice A. Howell
Assistant Examiner—Don Wong
Attorney, Agent, or Firm—Oblon, Spivak, McClelland, Maier & Neustadt

[57] ABSTRACT

An X-ray imaging apparatus has an X-ray imaging unit having an X-ray emitting source and an X-ray image recording member, and a rotatably supporting pedestal for rotatably supporting the X-ray imaging unit. A cam member is provided at one of the X-ray imaging unit and the rotatably supporting pedestal, a cam surface of which extends in the circumferential direction around the rotating center line of the X-ray imaging unit and an engaging recess is formed on the cam surface to be recessed inwardly in the radial direction relative to the rotating center line. The engaging mechanism is provided at the other of the X-ray imaging unit and the rotatably supporting pedestal to be in contact with the cam surface of the cam member and telescopically engaged with the engaging recess of the cam surface when the X-ray imaging unit is rotated.

11 Claims, 5 Drawing Sheets

X-RAY IMAGING APPARATUS

BACKGROUND OF THE INVENTION

1. Field of the Invention

The present invention relates to an X-ray imaging apparatus and, more particularly to an X-ray imaging apparatus in which an X-ray imaging unit having X-ray imaging means is rotatably supported by a rotatably supporting pedestal.

2. Description of the Related Art

Figure 1:
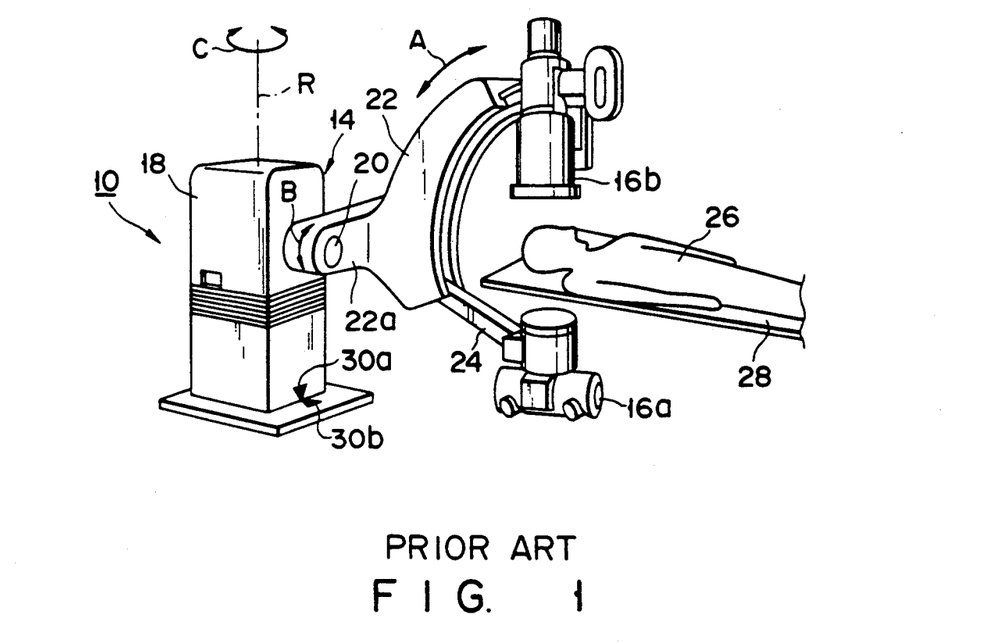
FIG. 1 is a perspective view schematically showing an arrangement of a conventional X-ray imaging apparatus, where an X-ray imaging unit rotatable on a rotatably supporting pedestal is disposed at an X-ray imaging position.

A conventional X-ray imaging apparatus 10 having an arrangement as mentioned above is schematically shown in FIG. 1. In FIG. 1, reference numeral 12 denotes a rotatably supporting pedestal installed, for example, on the floor of a building of a hospital, and numeral 14 denotes an X-ray imaging unit having X-ray imaging means 16a and 16b and rotatably supported on the rotatably supporting pedestal 12.

The X-ray imaging unit 14 has a vertically telescopically supporting post 18 rotatably supported on the rotatably supporting pedestal 12. A rotary drive source, not shown, having a rotatably driving shaft 20 protruding horizontally is stored in the vertically supporting post 18, and a coupling piece 22a protruding laterally from a partially circular-shaped arm guide 22 is attached to the rotatably driving shaft 20.

The arm guide 22 circumferentially movably supports a C-shaped supporting arm 24. The X-ray imaging means 16a and 16b are supported at both ends of the supporting arm 24.

One X-ray imaging means 16a is an X-ray emitting unit having an X-ray source, and the other X-ray imaging means 16b is an X-ray film cassette, a television camera, a movie camera, etc. the both two cameras being used together with an image intensifier. The television camera, the movie camera, and the X-ray film cassette are selectively used in response to its utility.

A bed 28 on which a patient 26 is laid is disposed near the conventional X-ray imaging apparatus 10 constructed as mentioned above. The bed 28 has a lower structure installed on the above-described floor and an upper structure mounted on the lower structure so as to be movable in its longitudinal direction with respect to the lower structure, on the upper structure the patient 26 being laid.

FIG. 1 shows the vertically imaging state of the X-ray imaging apparatus 10. In the bed 28, the upper structure on which the patient 26 is laid is so moved in its longitudinal direction relative to the lower structure that the end of the upper structure is disposed between the X-ray imaging means 16a and 16b at both ends of the supporting arm 24 on the arm guide 22 disposed at a vertical position.

In the X-ray imaging apparatus 10, when the supporting arm 24 is moved in the circumferential direction of the arm guide 22 as shown by bi-directional arrows A, the angle of the X-ray to be emitted to the patient 26 to cross the patient 26 between a pair of the X-ray imaging means 16a and 16b varies in the longitudinal direction of the bed 28 (i.e., in the longitudinal direction of the patient 26).

In the X-ray imaging apparatus 10, when the rotatably driving shaft 20 is rotated in both the directions shown by bi-directional arrows B by a rotary drive source, not shown, in the vertically supporting post 18, the angle of the X-ray to be emitted to the patient 26 between a pair of the X-ray imaging means 16a and 16b to cross the patient 26 varies in the lateral direction of the bed 28 (i.e., in the lateral direction of the patient 26).

In the X-ray imaging apparatus 10, the vertically supporting post 18 is vertically telescopically extended or contracted to contact or separate one X-ray imaging means 16a as an X-ray emitting unit with or from the patient 26.

When the X-ray imaging is not executed by the X-ray imaging apparatus 10, the vertically supporting post 18 is rotated from the position shown in FIG. 1 in either one of both directions shown by bi-directional arrows C around the rotational center line R of itself to move the arm guide 22 and the supporting arm 24 and hence a pair of the X-ray imaging means 16a and 16b to an X-ray imaging rest position, not shown, in which they are separated sidewisely from the bed 28 (i.e., sidewisely from the patient 26).

Markers 30a and 30b indicating that a pair of the X-ray imaging means 16a and 16b are disposed at the X-ray imaging position opposed to the patient 26 on the bed 28 as shown in FIG. 1 are provided on the lower end of the vertically supporting post 18 and the rotatably supporting pedestal 12.

An electromagnetic brake, not shown, is disposed between the lower end of the vertically supporting post 18 and the rotatably supporting pedestal 12, and the electromagnetic brake is used to hold the vertically supporting post 18 to the X-ray imaging position shown in FIG. 1. The rotation of the vertically supporting post 18 between the above-mentioned X-ray imaging rest position and the X-ray imaging position is conducted by man-power.

A work for disposing the X-ray imaging unit 14 at the X-ray imaging position in the conventional X-ray imaging apparatus requires a relatively long time, because the inertial moment of the X-ray imaging unit 14 is large so that it is difficult to so operate the X-ray imaging unit 14 by man-power as to bring a pair of markers 30a and 30b into coincidence. It is difficult to accurately stop the X-ray imaging unit 14, having a large inertial moment and once started moving, at the X-ray imaging position where the pair of markers 30a and 30b are coincident, and it is necessary to repeat the position correcting work.

If a relatively large force is applied to either one of the pair of X-ray imaging means 16a and 16b radially separated from the rotational center line R of the vertically supporting post 18 after the X-ray imaging unit 14 is disposed at the X-ray imaging position, the braking force of the electromagnetic clutch, not shown, might not oppose the rotary moment generated at the X-ray imaging unit 14 by the above relatively large force.

SUMMARY OF THE INVENTION

It is an object of the present invention to provide an X-ray imaging apparatus which can facilitate a work for accurately stopping an X-ray imaging unit at an X-ray imaging position and has a simple and inexpensive structure capable of positively holding the X-ray imaging unit at the X-ray imaging position.

In order to achieve the above object of the present invention, there is provided according to the present invention an X-ray imaging apparatus comprising an X-ray imaging unit having X-ray imaging means; a rotatably supporting pedestal for rotatably supporting the X-ray imaging unit; a cam member provided at one of the X-ray imaging unit and the rotatably supporting pedestal, having a cam surface extending circumferentially relative to the rotational center line of the X-ray imaging unit and formed on the cam surface thereof with an engaging recess recessed inwardly in the radial direction relative to the rotational center line of the X-ray imaging unit; and means, provided at the other of the X-ray imaging unit and the rotatably supporting pedestal, for contacting the cam surface of the cam member and detachably engaging with the engaging recess of the cam surface when the X-ray imaging unit is rotated.

In the X-ray imaging apparatus constructed according to the present invention as above, even the X-ray imaging unit rotated with the large inertial moment from the X-ray imaging rest position to the X-ray imaging position can be accurately stopped at the X-ray imaging position by engaging the engaging means with the engaging recess of the cam member. The X-ray imaging unit can be positively held at the X-ray imaging position against the rotary moment, generated at the X-ray imaging unit by an external force applied to the X-ray imaging means, by the above-mentioned engagement of the engaging means with the engaging recess of the cam member.

The above-mentioned large inertial moment is reduced by bringing the engaging means into contact with the cam surface of the cam member immediately before the engaging means is engaged with the engaging recess of the cam member. In this manner, a shock to be generated at the X-ray imaging unit upon stopping of the X-ray imaging unit at the X-ray imaging position by the above-mentioned engagement of the engaging means with the engaging recess of the cam member is reduced.

If the value of the above-mentioned large inertial moment is excessively large, the engaging means once engaged with the engaging recess of the cam member is disengaged to allow the X-ray imaging unit to further rotate. However, since the excessive inertial moment is remarkably reduced by the above-mentioned engagement and the contact of the engaging means with the cam face of the cam member generated immediately before the above-mentioned engagement, the X-ray imaging unit is, after the above-mentioned engagement is disengaged, immediately stopped rotating.

Since the rotation of the X-ray imaging unit with the excessive inertial moment is not abruptly stopped at the X-ray imaging position by the above-mentioned engagement, the X-ray imaging unit is protected against a shock generated in the X-ray imaging unit by the abrupt stop.

The arrangements of the cam member and the engaging means as described above can be simplified and reduced in its cost.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

Various embodiments and various modifications of the present invention will be described with reference to FIGS. 2 to 10.

DETAILED DESCRIPTION OF THE PREFERRED EMBODIMENTS

Figure 2:
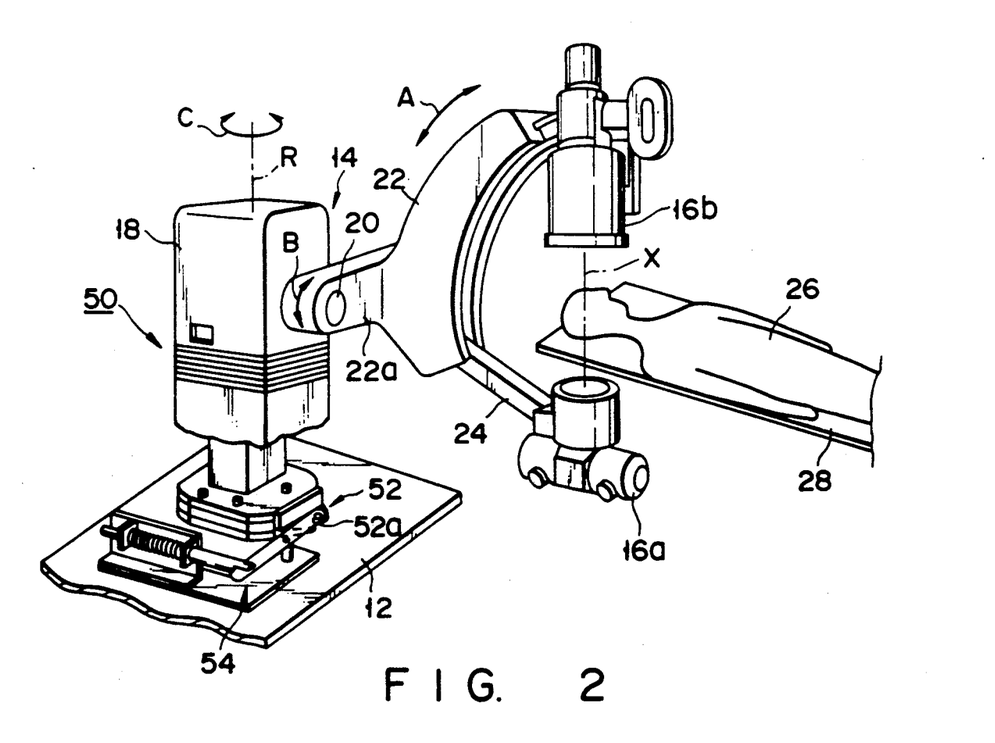
FIG. 2 is a perspective view schematically showing an arrangement of an X-ray imaging apparatus according to a first embodiment of the present invention.

FIG. 2 schematically shows an X-ray imaging apparatus 50 according to a first embodiment of the present invention. In FIG. 2, the same components as those of the above-mentioned conventional X-ray imaging apparatus 10 shown in FIG. 1 are designated by the same reference numerals, and a detailed description thereof will be omitted.

The X-ray imaging apparatus according to the first embodiment comprises, to readily and accurately dispose an X-ray imaging unit 14 from an X-ray imaging rest position to an X-ray imaging position rapidly, a cam plate 52 provided at a part on the outer periphery of the lower end portion of a vertically supporting post 18, and engaging means 54 provided on the upper surface of a rotatably supporting pedestal 12 to be detachably engaged with an engaging recess 52a formed on the cam surface of the cam plate 52, instead of markers 30a and 30b provided on the lower end portion of the vertically supporting post 18 of the X-ray imaging unit 14 and the upper surface of the rotatably supporting pedestal 12 in the above-described conventional X-ray imaging apparatus in FIG. 1.

In FIG. 2, the X-ray imaging unit 14 of the X-ray imaging apparatus 50 is disposed at an X-ray imaging position in which an X-ray "X" to be emitted between X-ray imaging means 16a and 16b is passed through an X-ray imaging position of a patient 26 on a bed 28.

In FIG. 2, the cam plate 52 and the engaging means 54 are drawn in a larger scale than the X-ray imaging unit 14 to clarify the drawing. The cam plate 52 and the engaging means 54 are exposed in an outer space, but they are originally covered by a skirt member, not shown, provided at the lower end portion of the vertically supporting post 18.

Figure 3:
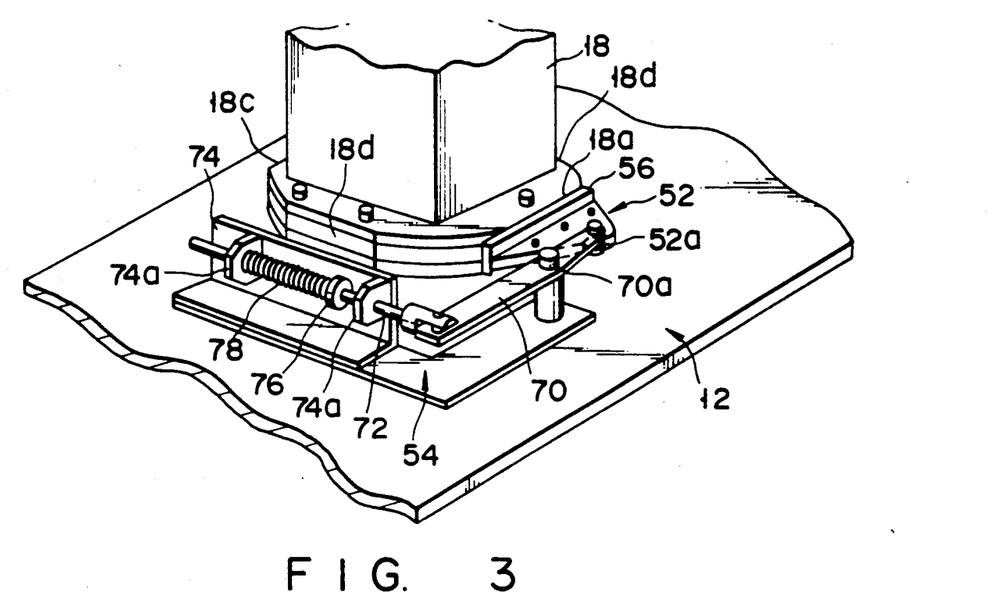
FIG. 3 is a schematic perspective view showing in a large scale a cam plate provided at a part of the outer peripheral surface of the lower end portion of a vertically supporting post of an X-ray imaging unit of the X-ray imaging apparatus in FIG. 2 and engaging means provided on the upper surface of a rotatably supporting pedestal to be detachably engaged with an engaging recess formed on a cam surface of the cam plate.
Figure 4:
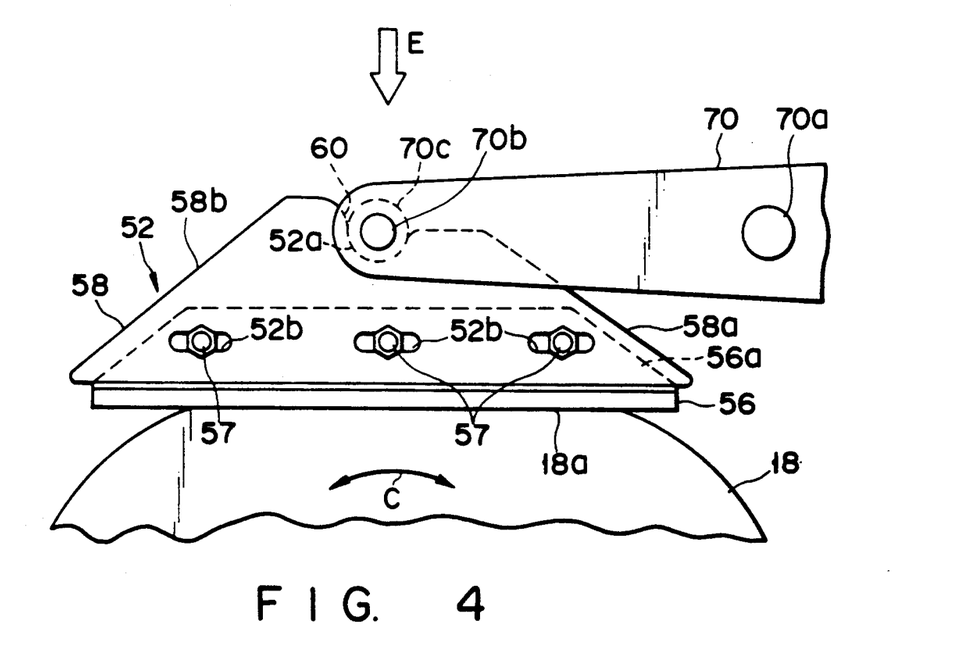
FIG. 4 is a schematic plan view showing in a large scale the shape of the cam plate in FIG. 3 and the structure of the end of the engaging means detachably engaged with the engaging recess formed on the cam surface of the cam plate.

In FIG. 3, the lower end portion of the vertically supporting post 18, the cam plate 52 and the engaging means 54, both of the latter two being disposed around the lower end portion of the post 18, are schematically shown in a large scale, and the structure of the engaging means 54 is particularly shown well. In FIG. 4, the shape of the cam plate 52 and the structure of the end of the engaging means 54 detachably engaged with the engaging recess 52a formed on the cam surface of the cam plate 52 are schematically shown in a large scale.

As shown in FIGS. 3 and 4, a cam plate fastening member 56 of L shape in section is fixed to a part of the outer peripheral surface of the lower end portion of the vertically supporting post 18 by known fastening means such as a bolt, etc. In this embodiment, four positions 18a, 18b, 18c and 18d isolated at an equal interval on the outer peripheral surface of the lower end portion of the vertically supporting post 18 are flatly finished along tangential lines at the respective positions to form supporting surfaces for the cam plate fastening member 56.

As shown in FIG. 4, a plurality of screw holes are formed in the upper surface of the horizontally supporting portion 56a of the cam plate fastening member 56 so as to be disposed at an equal interval along the tangential direction of the corresponding supporting surface 18a on the outer peripheral surface of the lower end portion of the vertically supporting post 18.

The cam plate 52 has a plurality of bolt inserting holes 52b corresponding to the plurality of screw holes of the cam plate fastening member 56, and is fixed to the upper surface of the horizontally supporting portion 56a of the cam plate fastening member 56 by screwing the tip end portions of the bolts 57 inserted in the respective bolt inserting holes 52b into the corresponding screw holes of the cam plate fastening member 56.

The plurality of bolt inserting holes 52b are elongated in the tangential direction of the supporting surface 18a of the vertically supporting post 18 so that the cam plate 52 is movable in the tangential direction at a distance corresponding to the length of the bolt inserting hole 52b in its longitudinal direction by weakening the clamping of the bolts 57.

The peripheral surface of the cam plate 52 extending along the circumferential direction of the vertically supporting post 18 is formed as a cam surface 58, and the cam surface 58 radially outwardly protrudes at the center thereof in the tangential direction. The engaging recess 52a is formed on the outer protruding end of the cam surface 58 of the cam plate 52.

The cam surface 58 is composed of a clockwise end portion 58a disposed at the front end side in the clockwise direction around the vertically supporting post 18 and a counterclockwise end portion 58b disposed at the front end side in the counterclockwise direction around the vertically supporting post 18, and the engaging recess 52a is a boundary between the two end portions 58a, 58b. The protruding height of the clockwise end portion 58a is, as shown in FIG. 4, smaller than that of the counterclockwise end portion 58b. More specifically, the depth of the engaging recess 52a is so formed that the side of the counterclockwise end portion 58b is larger than that of the clockwise end portion 58a so that the protruding end of the counterclockwise end portion 58b functions as a stop 60.

The engaging means 54 has, as shown in FIGS. 3 and 4, a lever 70 extending tangentially from the protruding end of the cam surface 58 (i.e., the engaging recess 52a). The lever 70 is disposed horizontally with respect to the upper surface of the rotatably supporting pedestal 12, and an intermediate portion 70a thereof is supported on the upper surface of the rotatably supporting pedestal 12 so as to be rotatable in a parallel manner with respect to the upper surface.

An engaging pin 70b is fixed to one end portion of the lever 70 disposed near the engaging recess 52a of the cam member 52, and engaged with the engaging recess 52 through a roller 70c supported on the engaging pin 70b so as to be rotatable concentrically thereto.

One end of a link lever 72 extending parallel to the upper surface of the rotatably supporting pedestal 12 from the other end of the lever 70 to partly surround the peripheral surface of the vertically supporting post 18 in cooperation with the lever 70 is coupled, as shown particularly well in FIG. 3, to the other end portion of the lever 70 disposed remotely from the engaging recess 52a of the cam member 52. One end portion of the link lever 72 is rotatable in a horizontal plane to the upper surface of the rotatably supporting pedestal 12 with respect to the other end portion of the lever 70, and the other end portion of the lever 70 is movable slightly in the longitudinal direction of itself with respect to one end portion of the link lever 72.

The link lever 72 penetrates two brackets 74a of a link lever supporting member 74 fixed to the upper surface of the rotatably supporting pedestal 12 at two positions isolated from each other in the longitudinal direction of the link lever 72, and is supported by the two brackets 74a so as to be slidable in the longitudinal direction of itself.

A stopper 76 is fixed to the link lever 72 between the two brackets 74a of the link lever supporting member 74, and a compression coil spring 78 is wound on the link lever 72 between the bracket 74a remote from the lever 70 and the stopper 76.

The compression coil spring 78 urges the link lever 72 toward the other end portion of the lever 70. The link lever 72 urged by the compression coil spring 78 urges the lever 70 so that the roller 70d of one end portion of the lever 70 is moved inwardly in the radial direction of the vertically supporting post 18 (shown by an arrow E in FIG. 4), thereby holding the engagement of the roller 70c with the engaging recess 52 of the cam plate 52.

Figure 5:
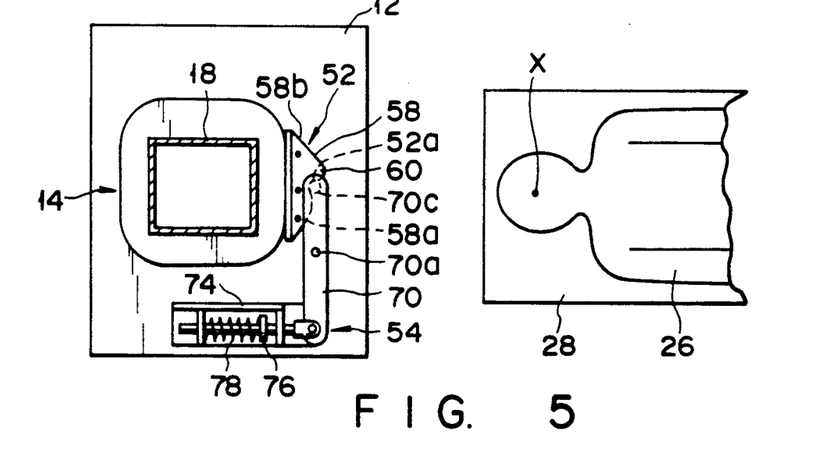
FIG. 5 is a schematic plan view showing the mutual action of the cam plate of the lower end portion of the vertically supporting post and the engaging means of the upper surface of the rotatably supporting pedestal when the X-ray imaging unit of the X-ray imaging apparatus is disposed at the X-ray imaging position.

In the X-ray imaging apparatus 50 according to one embodiment of the present invention and constructed as described above, when the X-ray imaging unit 14 is located at the X-ray imaging position as shown in FIG. 2, the roller 70c of one end portion (free end portion) of the lever 70 of the engaging means 54 on the rotatably supporting pedestal 12 is held, as shown particularly well in FIG. 5, in the engaging state with the engaging recess 52a of the cam plate 52 of the outer peripheral surface of the lower end portion of the vertically supporting post 18 of the X-ray imaging unit 14 by the urging force of the compression coil spring 78 of the engaging means 54.

To move the X-ray imaging unit 14 from the X-ray imaging position shown in FIGS. 2 and 5 to the X-ray imaging rest position in which the X-ray "X" to be emitted between the pair of X-ray imaging means 16a and 16b of the X-ray imaging unit 14 cannot pass a patient 26 on the bed 28, at least one of the arm guide 22, the supporting arm 24 and the X-ray imaging means 16a and 16b of the X-ray imaging unit 14 are pushed in the counterclockwise direction around the rotating center line R of the vertically supporting post 18. The roller 70c of the free end portion of the lever 70 of the engaging means 54 is separated from the engaging recess 52a of the cam plate 52 onto the clockwise end portion 58a having a lower protruding height of the cam surface 58 by the above described pushing force, and the X-ray imaging unit 14 rotates in the counterclockwise direction from the X-ray imaging position shown in FIGS. 2 and 5 to the X-ray imaging rest position as shown in FIG. 6.

Figure 6:
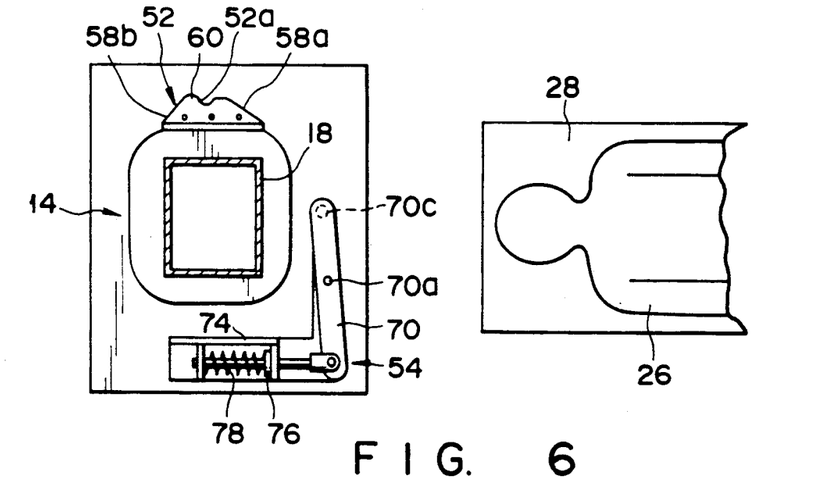
FIG. 6 is a schematic plan view showing relative positional relationship between the cam plate of the lower end portion of the vertically supporting post and the engaging means of the upper surface of the rotatably supporting pedestal when the X-ray imaging unit of the X-ray imaging apparatus in FIG. 2 is disposed at the X-ray imaging rest position.

To return the X-ray imaging unit 14 from the X-ray imaging rest position shown in FIG. 6 to the X-ray imaging position shown in FIGS. 2 and 5, at least one of the arm guide 22, the supporting arm 24 and the X-ray imaging means 16a and 16b of the X-ray imaging unit 14 are pushed in the clockwise direction around the rotating center line R of the vertically supporting post 18. The vertically supporting post 18 of the X-ray imaging unit 14 is rotated in the clockwise direction by the pushing force. The cam plate 52 on the vertically supporting post 18 rotating in the clockwise direction brings the clockwise end portion 58a of the cam surface 58 into contact with the roller 70c of the free end portion of the lever 70 of the engaging means 54 to thereby weaken the above-described pushing force, and the roller 70c brought into contact with the clockwise end portion 58a of the cam surface 58 of the cam plate 52 is pushed outwardly in the radial direction of the vertically supporting post 18 against the urging force of the compression coil spring 78 of the engaging means 54. The roller 70c is then engaged with the engaging recess 52a of the cam surface 58 of the cam plate 53 so that the X-ray imaging unit 14 is stopped at the X-ray imaging position shown in FIGS. 2 and 5.

The protruding end 60 of the counterclockwise end portion 58d having a high protruding height of the cam plate 52 prevents the roller 70c entered from the side of the clockwise end portion 58a having a lower protruding height into the engaging recess 52a from moving out from the engaging recess 52a to the side of the counterclockwise end portion 58b.

However, if the pushing force applied to the X-ray imaging unit 14 to move the X-ray imaging unit 14 from the X-ray imaging rest position to the X-ray imaging position is excessively large, the roller 70c entered from the side of the clockwise end portion 58a having a lower protruding height into the engaging recess 52a overrides the protruding end 60 of the counter clockwise end portion 58b onto the side of the counterclockwise end portion 58b to be moved out from the engaging recess 52a.

If it is assumed that the roller 70c is collided with the protruding end 60 of the counterclockwise end portion 58b in the engaging recess 52a so that the rotation of the X-ray imaging unit 14 abruptly stops against the excessive pushing force as described above, the excessive impact force is applied to the X-ray imaging unit 14, so that the structure of the X-ray imaging unit 14 is fluctuated by the excessive impact force to cause the X-ray imaging unit 14 to readily be troubled, or the cam plate 52 and the engaging means 54 to easily be damaged. In order to surely prevent the X-ray imaging unit 14, the cam plate 52 and the engaging means 54 from being troubled or damaged by the excessive impact force, these unit and/or the members must be formed by using high class materials or in a rigid structure, so that the profile of the X-ray imaging apparatus 50 is increased, and the production price is raised.

The moving out of the roller 70c from the engaging recess 52a of the cam plate 52 onto the counterclockwise end portion 58b caused by the application of the excessive pushing force to the X-ray imaging unit 14 effectively prevents the X-ray imaging unit 14 from being troubled and the cam plate 52 and the engaging means 54 from being damaged caused by the abrupt stop of rotation of the X-ray imaging unit 14, which frees the unit and the members from being needing to be formed of high class materials and in a rigid structure, and effectively prevents the profile of the X-ray imaging apparatus 50 from increasing and the production cost from rising.

Figure 7:
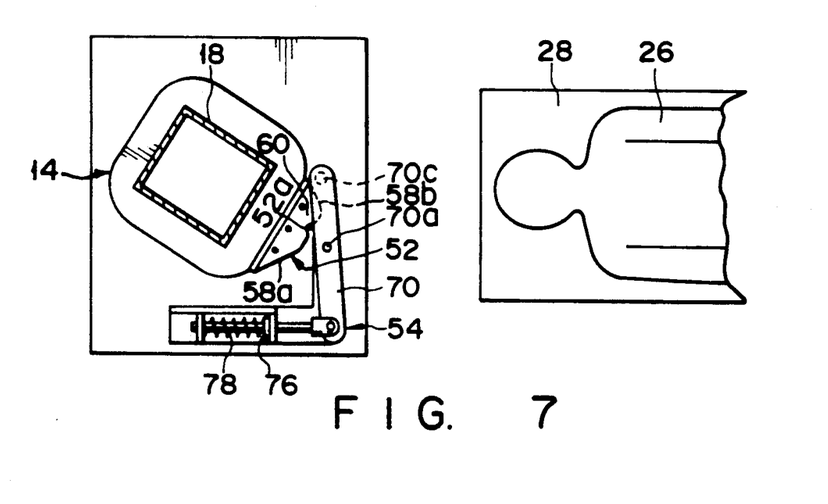
FIG. 7 is a schematic plan view showing the mutual action between the cam plate of the lower end portion of the vertically supporting post and the engaging means of the upper surface of the rotatably supporting pedestal when a rotary force applied to the X-ray imaging unit for rotating the X-ray imaging unit of the X-ray imaging apparatus in FIG. 2 from the X-ray imaging rest position shown in FIG. 6 to the X-ray imaging position shown in FIG. 5 is excessive.

In the X-ray imaging unit 14 after the roller 70c is moved out from the engaging recess 52a of the cam plate 52, most of the rotary inertial moment is erased until the roller 70c is moved out from the engaging recess 52a, and the clockwise rotation thereof is stopped soon as shown in FIG. 7.

Figure 8:
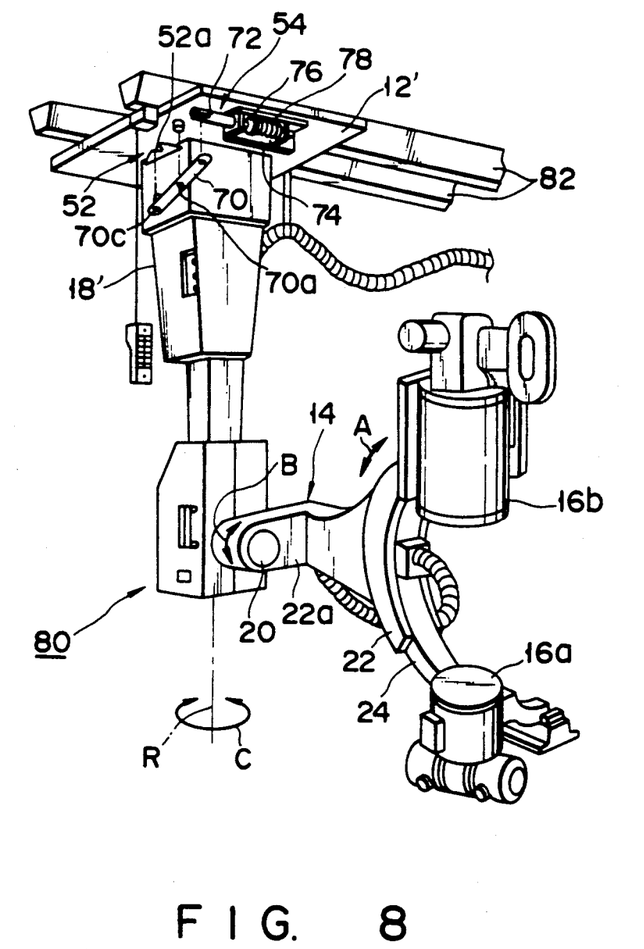
FIG. 8 is a perspective view schematically showing an arrangement of an X-ray imaging apparatus according to a second embodiment of the present invention.

FIG. 8 schematically shows an X-ray imaging apparatus 80 according to a second embodiment of the present invention. In FIG. 8, the same components as those of the conventional X-ray imaging apparatus 10 described above in FIG. 1 are designated by the same reference numerals, and a detailed description thereof will be omitted.

The X-ray imaging apparatus 80 of this embodiment is a ceiling supported type. A rotatably supporting pedestal 12' for an X-ray imaging unit 14 is supported by guide rails 82 fixed to the ceiling of a building, such as a hospital building, to be movable along the guide rails 82. The vertically supporting post 18' of the X-ray imaging unit 14 is rotatably supported at the upper end thereof to the rotatably supporting pedestal 12', and a rotary drive source, not shown, having a horizontally rotatable shaft 20 is stored in the lower end portion of the vertically supporting post 18' of the X-ray imaging unit 14.

In this embodiment, engaging means 54 having a lever 70, a link lever 72 and a compression coil spring 78 is so attached to the lower surface of the rotatably supporting pedestal 12' as to partly surround the upper end portion of the outer peripheral surface of the vertically supporting post 18'. A cam plate 52 is detachably attached to a part of the outer peripheral surface of the upper end portion of the vertically supporting post 18'.

Even in this embodiment, the engaging means 54 on the lower surface of the rotatably supporting pedestal 12' and the cam plate 52 on the outer peripheral surface of the upper end portion of the vertically supporting post 18' may be covered with a cover, not shown, to be attached to the outer peripheral surface or the lower surface thereof.

The engaging means 54 and the cam plate 52 function similarly to those of the above-mentioned first embodiment.

Figure 9:
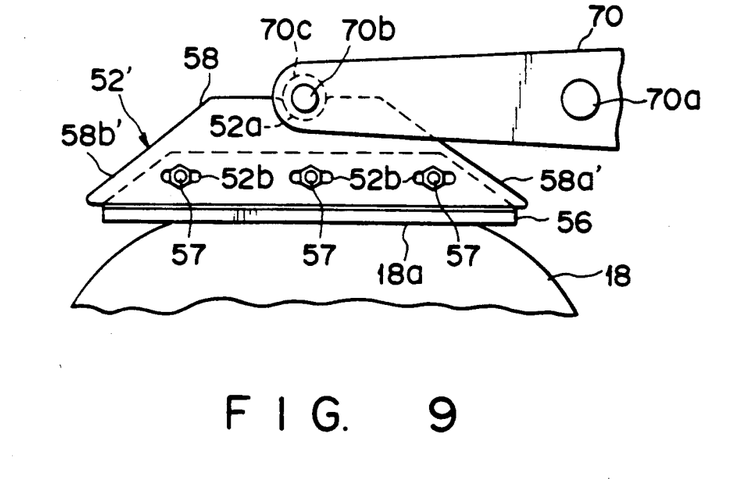
FIG. 9 is a plan view schematically showing in a large scale a first modification of a cam plate.

FIG. 9 shows a first modification of the above-mentioned cam plate 52. In the cam plate 52' of the first modification, a clockwise end portion 58a' and a counterclockwise end portion 58b' of the cam face 58 are set in the same protruding height. When the cam plate 52' according to the modification is employed, X-ray imaging rest positions can be set at both sides of the X-ray imaging position in the circumferential direction of the vertically supporting post. More specifically, the X-ray imaging unit can be disposed readily and accurately to the X-ray imaging position from any of two X-ray imaging rest positions disposed at both sides of the X-ray imaging positions in the circumferential direction of the vertically supporting post.

Figure 10:
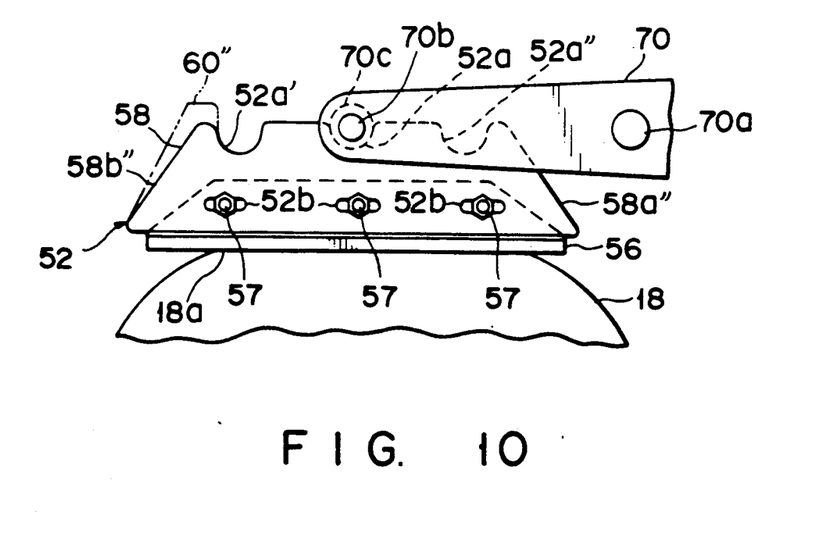
FIG. 10 is a plan view schematically showing in a large scale a second modification of the cam plate.

FIG. 10 shows a second modification of the above-mentioned cam plate 52. In the cam plate 52" of the second modification, three engaging recesses 52a, 52a' and 52a" are formed at a predetermined interval in the circumferential direction of the vertically supporting post 18 at the central protruding end portion of the cam surface 58 of the cam plate 52". In this embodiment, the protruding heights of the clockwise end portion 58a" and the counterclockwise end portion 58b" of the cam surface 58 are set in the same as those of the portions of the cam surface 58 located between the three engaging recesses 52a, 52a' and 52a", but the protruding height of the protruding end 60" of the counterclockwise end portion 58b" may be formed higher than the protruding height of other portions described above as shown by a two-dot chain line in FIG. 10.

When the cam plate 52" according to the second modification is employed, the three X-ray imaging positions located close to each other can be readily and accurately set.

Additional advantages and modifications will readily occur to those skilled in the art. Therefore, the invention in its broader aspects is not limited to the specific details, and representative devices, shown and described. Accordingly, various modifications may be made without departing from the spirit or scope of the general inventive concept as defined by the appended claims and their equivalents.

What is claimed is:

1. An X-ray imaging apparatus comprising:
   an X-ray imaging unit having X-ray imaging means;
   a rotatable support for rotatably supporting the X-ray imaging unit;
   a cam member provided at one of the X-ray imaging unit or the rotatable support, having a cam surface extending circumferentially relative to a rotational center line of the X-ray imaging unit and formed on the cam surface thereof with an engaging recess recessed inwardly in the radial direction relative to the rotational center line of the X-ray imaging unit;
   wherein the cam surface of said cam member radially externally protrudes at one of two regions located at both sides of said engaging recess in the circumferential direction as approaching from a position remote from said engaging recess toward said engaging recess in the circumferential direction;
   wherein the cam surface of said cam member radially externally protrudes at the other of the two regions located at both sides of said engaging recess in the circumferential direction as approaching from a position remote from said engaging recess toward said engaging recess in the circumferential direction; and
   wherein the two regions on the cam surface located on both sides of said engaging recess of said cam member are so formed that one is larger at a protruding distance in the radial direction than the other;
   means, provided at the other of the X-ray imaging unit or the rotatable support, for contacting the cam surface of the cam member and detachably engaging with the engaging recess of the cam surface when the X-ray imaging unit is rotated.

2. The X-ray imaging apparatus according to claim 1, wherein said cam member is detachable from either one of the X-ray imaging unit and the rotatably supporting pedestal at a plurality of positions isolated from each other in the circumferential direction thereof.

3. The X-ray imaging apparatus according to claim 1, wherein said cam member has a plurality of engaging recesses at a plurality of positions isolated from each other in the circumferential direction on the cam surface.

4. The X-ray imaging apparatus according to claim 1, wherein said engaging means includes a link mechanism having at one end thereof an engaging pin to be in contact with the cam surface of said cam member and engaged with said engaging recess, and means for urging the link mechanism to move inwardly the engaging pin in the radial direction.

5. The X-ray imaging apparatus according to claim 4, wherein said link mechanism includes a lever having an engaging pin at one end thereof and rotatably attached at an intermediate portion thereof to the other of the X-ray imaging unit and the rotatably supporting pedestal, and said urging means is coupled to the other end of the lever and so arranged as to extend in a direction crossing the lever and to oppose the other of the X-ray imaging unit and the rotatably supporting pedestal.

6. The X-ray imaging apparatus according to claim 4, wherein said engaging pin so supports a rotatable roller as to be concentrically rotatable.

7. An X-ray imaging apparatus comprising:
   an X-ray imaging unit having X-ray imaging means;
   a rotatable support for rotatably supporting the X-ray imaging unit;
   a cam member provided at one of the X-ray imaging unit or the rotatable support, having a cam surface extending circumferentially relative to a rotational center line of the X-ray imaging unit and formed on the cam surface thereof with an engaging recess recessed inwardly in the radial direction relative to the rotational center line of the X-ray imaging unit;
   wherein the cam surface of said cam member radially externally protrudes at one of two regions located at both sides of said engaging recess in the circumferential direction as approaching from a position remote from said engaging recess toward said engaging recess in the circumferential direction;
   wherein the cam surface of said cam member radially externally protrudes at the other of two regions located at both sides of said engaging recess in the circumferential direction as approaching from a position remote from said engaging recess toward said engaging recess in the circumferential direction; and wherein the two regions on the cam surface located on both sides of said engaging recess of said cam member are so formed that one is larger at a protruding distance in the radial direction than the other;

means, provided at the other of the X-ray imaging unit or the rotatable support, for contacting the cam surface of the cam member and detachably engaging with the engaging recess of the cam surface when the X-ray imaging unit is rotated, wherein said engaging means includes a link mechanism having at one end thereof an engaging pin to be in contact with the cam surface of said cam member and engaged with said engaging recess, and means for urging the link mechanism to inwardly move the engaging pin in the radial direction.

8. The X-ray imaging apparatus according to claim 7, wherein said cam member is detachable from either one of the X-ray imaging unit and the rotatably supporting pedestal at a plurality of positions isolated from each other in the circumferential direction thereof.

9. The X-ray imaging apparatus according to claim 7, wherein said cam member has a plurality of engaging recesses at a plurality of positions isolated from each other in the circumferential direction on the cam surface.

10. The X-ray imaging apparatus according to claim 7, wherein said link mechanism includes a lever having an engaging pin at one end thereof and rotatably attached at an intermediate portion thereof to the other of the X-ray imaging unit and the rotatably supporting pedestal, and said urging means is coupled to the other end of the lever and so arranged so as to extend in a direction crossing the lever and to oppose the other of the X-ray imaging unit and the rotatably supporting pedestal.

11. The X-ray imaging apparatus according to claim 7, wherein said engaging pin so supports a rotatable roller as to be concentrically rotatable.

* * * * *